United States Patent [19]

Cooper

[11] Patent Number: 4,936,309

[45] Date of Patent: Jun. 26, 1990

[54] DUAL PHYSIOLOGICAL RATE MEASUREMENT INSTRUMENT

[75] Inventor: Tommy G. Cooper, Houston, Tex.

[73] Assignee: The United States of America as represented by the Administrator, National Aeronautics and Space Administration, Washington, D.C.

[21] Appl. No.: 183,475

[22] Filed: Apr. 15, 1988

Related U.S. Application Data

[63] Continuation of Ser. No. 585,627, Mar. 7, 1984, abandoned, which is a continuation of Ser. No. 394,343, Jul. 1, 1982, abandoned.

[51] Int. Cl.$^5$ ............................................. A61B 5/0205
[52] U.S. Cl. ..................................... 128/671; 128/689; 128/706; 128/716; 331/1 R; 331/17; 331/25
[58] Field of Search ............... 128/687, 689, 706, 671, 128/716; 324/78; 331/1 A, 1 R, 17, 25

[56] References Cited

U.S. PATENT DOCUMENTS

| | | | |
|---|---|---|---|
| 4,182,315 | 1/1980 | Vas et al. | 128/687 |
| 4,256,008 | 3/1981 | Ryon | 324/78 R |
| 4,414,504 | 11/1983 | Kennedy | 324/78 R |

OTHER PUBLICATIONS

Technical Specifications for 4046, RCA Databook, 1980, pp. 176–181.

Primary Examiner—Kyle L. Howell
Assistant Examiner—John C. Hanley
Attorney, Agent, or Firm—Russell E. Schlorff; John R. Manning; Edward K. Fein

[57] ABSTRACT

The object of the invention is to provide an instrument for converting a physiological pulse rate into a corresponding linear output voltage.

The instrument (1) which accurately measures the rate of an unknown rectangular pulse wave (9) over an extended range of values, comprises a phase-locked loop (8) including a phase comparator (4), a filtering network (6), and a voltage-controlled oscillator (5), arranged in cascade. The phase comparator has a first input (10) responsive to the pulse wave and a second input (11) responsive to the output signal of the voltage-controlled oscillator. The comparator (4) provides a signal dependent on the difference in phase and frequency between the signals appearing on the first and second inputs. A high-input impedance amplifier (16) accepts an output from the filtering network and provides an amplified output DC signal to a utilization device (16) for providing a measurement of the rate of the pulse wave.

2 Claims, 2 Drawing Sheets

DUAL PHYSIOLOGICAL RATE MEASUREMENT INSTRUMENT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; USC 2457).

This application is a continuation of application Ser. No. 585,627, filed 3/7/84 abandoned which is a continuation of Ser. No. 394,343, filed 7/01/82 abandoned.

TECHNICAL FIELD

The invention relates to an instrument whose basic function is to convert one or a pair of physiological pulse rates to one or a pair of corresponding linear output voltages suitable for monitoring or recording purposes.

When measuring basic physiological phenomena, such as heart beat rate or breath cycle rate, it is essential that the instrument have a fast response time, good linearity, and stability over its full operating range. It is also desirable that the circuit employs relatively inexpensive and readily available digital and analog integrated circuits. In addition, the circuitry must be reliable and retain its accuracy over wide changes in environmental conditions, such as are encountered in portable instruments used in remote locations or under space flight conditions.

BACKGROUND ART

Numerous techniques have been used and proposed for measuring physiological rates. U.S. Pat. No. 4,066,069 relates to a system for detecting differences between a pre-recorded, normal, reference pulse wave obtained from an electrocardiogram (ECG) and a measured ECG pulse wave from the same subject. A phase-lock loop (PLL) is used to synchronize the rate of the reference ECG wave with the rate of the measured ECG wave to obtain a comparison between them. Specifically, in this patented system a reference heart beat signal is recirculated for comparison with an actual heart beat signal. First and second voltages are produced having amplitudes respectively representing the rate of the reference heart beat and the rate of the actual heart beat. A voltage-controlled oscillator (VCO) produces a signal output having a frequency dependent upon the difference between the first and second voltages. This VCO output signal is used to synchronize the reference heart beat signal with the actual heart beat signal.

U.S. Pat. No. 4,202,340 shows a circuit for monitoring heart activity. The circuit utilizes a sensed cardiac parameter indicative of the operation of the heart being monitored and generates a probability density function from the sensed parameter. The probability density function is analyzed and its shape is compared with the shape of a probability density function indicative of normal cardiac function. The differences in shape are used to indicate abnormal cardiac function of the heart being monitored.

U.S. Pat. No. 4,063,551 is concerned with sensing blood pulses by emitting an infrared light toward a blood vessel and monitoring the relative absorbtion of the light in the blood stream to indicate the timing of blood pulses.

DISCLOSURE OF THE INVENTION

It is a specific object of the present invention to provide an instrument capable of measuring simultaneously or separately the heart beat rate (HR) and the respiratory cycle rate (RESP) of the same subject. The instrument is fast responsive, relatively inexpensive, and utilizes a digital integrated circuit (IC) COSMOS PLL that is commercially available and is particularly suitable for making bio-medical measurements.

This PLL features a phase comparator consisting of a digital, positive edge-controlled memory network which permits the PLL to be locked in phase and frequency over the full, relatively-large, operating frequency range of its VCO.

BRIEF DESCRIPTION OF DRAWINGS

The details of the invention will be described in connection with the accompanying drawings, in which.

BEST MODE FOR CARRYING OUT THE INVENTION

Figure 1:
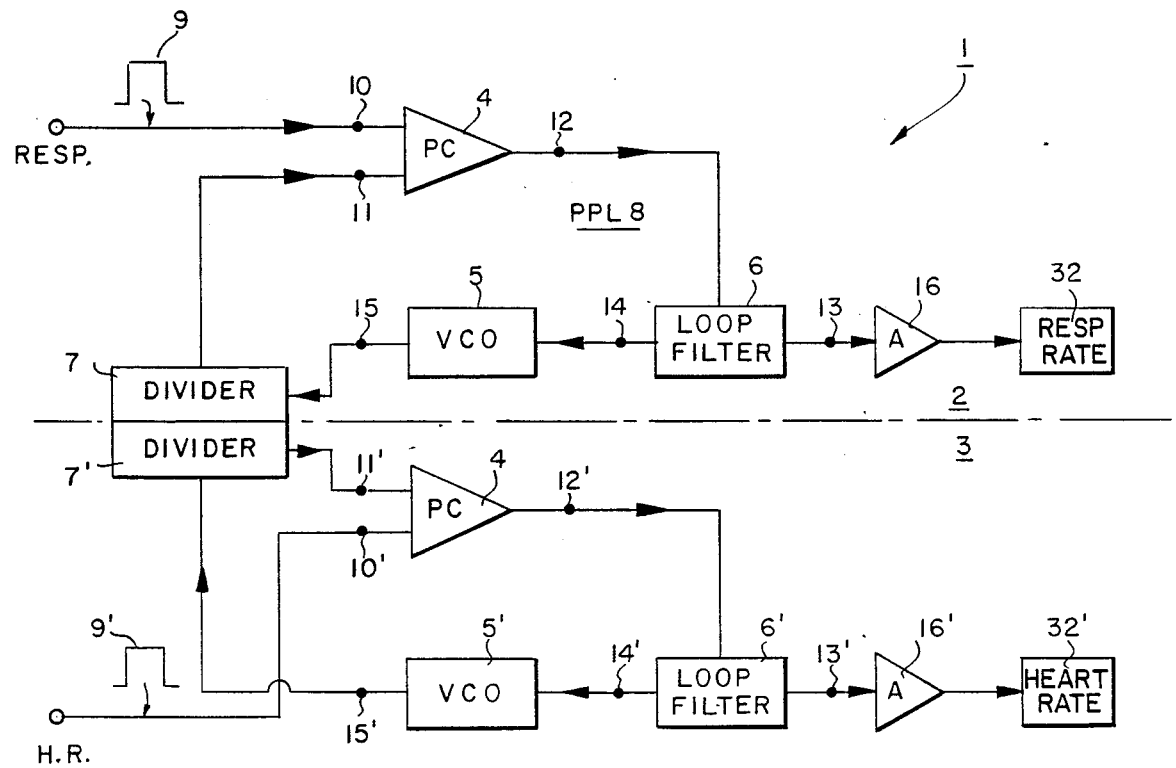
FIG. 1 is a block diagram of the instrument.

Referring to the drawing, there is shown a dual measurement instrument 1, constructed in accordance with the invention, which comprises two channels 2 and 3, each having a phase comparator (PC) 4, a voltage-controlled oscillator (VCO) 5, a loop filter (LF) 6, and a frequency divider 7, all cascaded around a phase-lock loop (PLL) 8.

After lengthy experimental investigations, it was determined that by using a PLL and properly selecting the parameters of the components added to the PLL, it is possible to convert physiological pulse rates under optimum linearity and response time.

Instrument 1 receives a pair of rectangular wave signals 9, 9' which are derived from a pneumogram and cardiogram, respectively. These rectangular wave signals are of constant amplitude but they can vary in frequency or pulse rate.

Signal 9 represents the respiration cycle rate of a subject, and signal 9' represents his heart beat rate. Signal 9 is converted in channel 2, and signal 9' is converted in channel 3.

Signal 9 is applied to one input 10 of the PC 4. The output of divider 7 is applied to the other input 11 of PC 4.

The function of PC 4 is to compare the phases and frequencies of the rectangular wave signals appearing at its input terminals 10 and 11 and to produce at its output terminal 12 an output signal having a DC voltage indicative of their phase and frequency error or deviation. Under static conditions, the phase and frequency error between the signals appearing at the two input terminals 10 and 11 is substantially zero which is taken as the reference condition. Under dynamic conditions, the instantaneous phase and frequency error between the two signals appearing on inputs 10 and 11 fluctuates, and the output of PC 4 on its output terminal 12 is a rectangular wave signal having a DC component and an AC component. The DC component is proportional to the phase and frequency error or deviation from 0°.

Due to the action of the PLL 8, the two input rectangular waves appearing on inputs 10 and 11 are forced to be in phase and to have the same frequency. As a consequence, the voltage on output terminal 12 of PC 4 is proportional to the input phase and frequency error to the PC 4 within the full range of instrument 1.

In sum, in the absence of an input signal 9, the DC voltage at output terminal 12 is substantially zero. When signal 9 advances in frequency, then the corresponding phase and frequency error is substantially instantaneously detected by PC 4 to provide a DC component to its output terminal 12 having an amplitude which is linearly related to the magnitude of this phase error. The detected signal from the PC 4 appearing at terminal 12 is applied to the loop filter (LF) 6.

Essentially, the function of LF 6 is to pass therethrough to its first output 13 only the DC component which appears at the output 12 from the PC 4, while blocking as much as possible the AC component, and to establish the dynamic conditions necessary for proper phase and frequency tracking by the PLL 8. The second output 14 from the LF 6 receives a signal which is applied to the VCO 5.

The function of VCO 5 is to change the frequency and phase of the signal appearing at its output terminal 15 by a magnitude and in a direction so as to eliminate the phase and frequency error originally responsive for the creation of the DC component at output terminal 12 from PC 4. The frequency of the signal appearing at terminal 15 is relatively low. Divider 7 divides this signal by ten which allows VCO 5 to operate at a much higher frequency. Divider 7 is connected between terminals 11 and 15.

Figure 2:
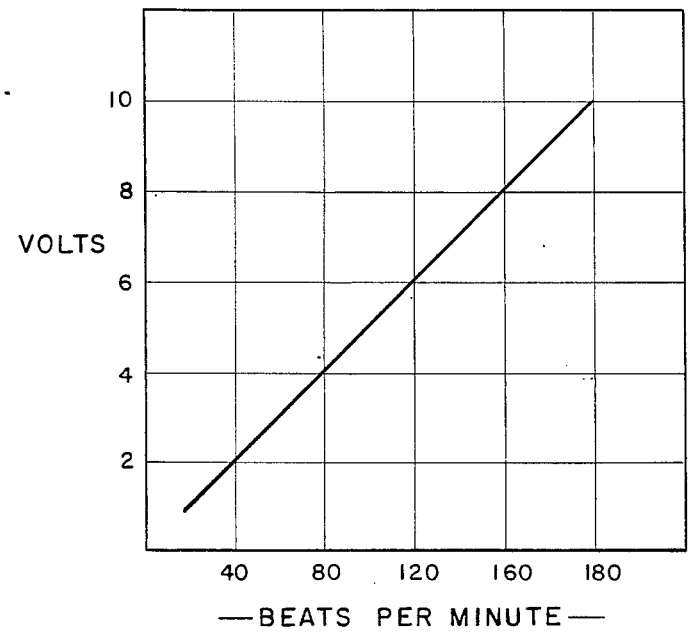
FIG. 2 is a graph showing the linearity between the instrument's output voltage and the input pulse rate.

Thus, the PLL 8 translates substantially linearly and instantaneously the incoming pulse wave 9 into an intelligence DC voltage having deviations which are substantially proportional to the frequency deviations of signal 9 (FIG. 2). It follows that the signal at terminal 13 represents the desired intelligence signal.

The intelligence signal can be taken directly from terminal 13 but preferably it is first amplified by an amplifier 16.

Figure 3:
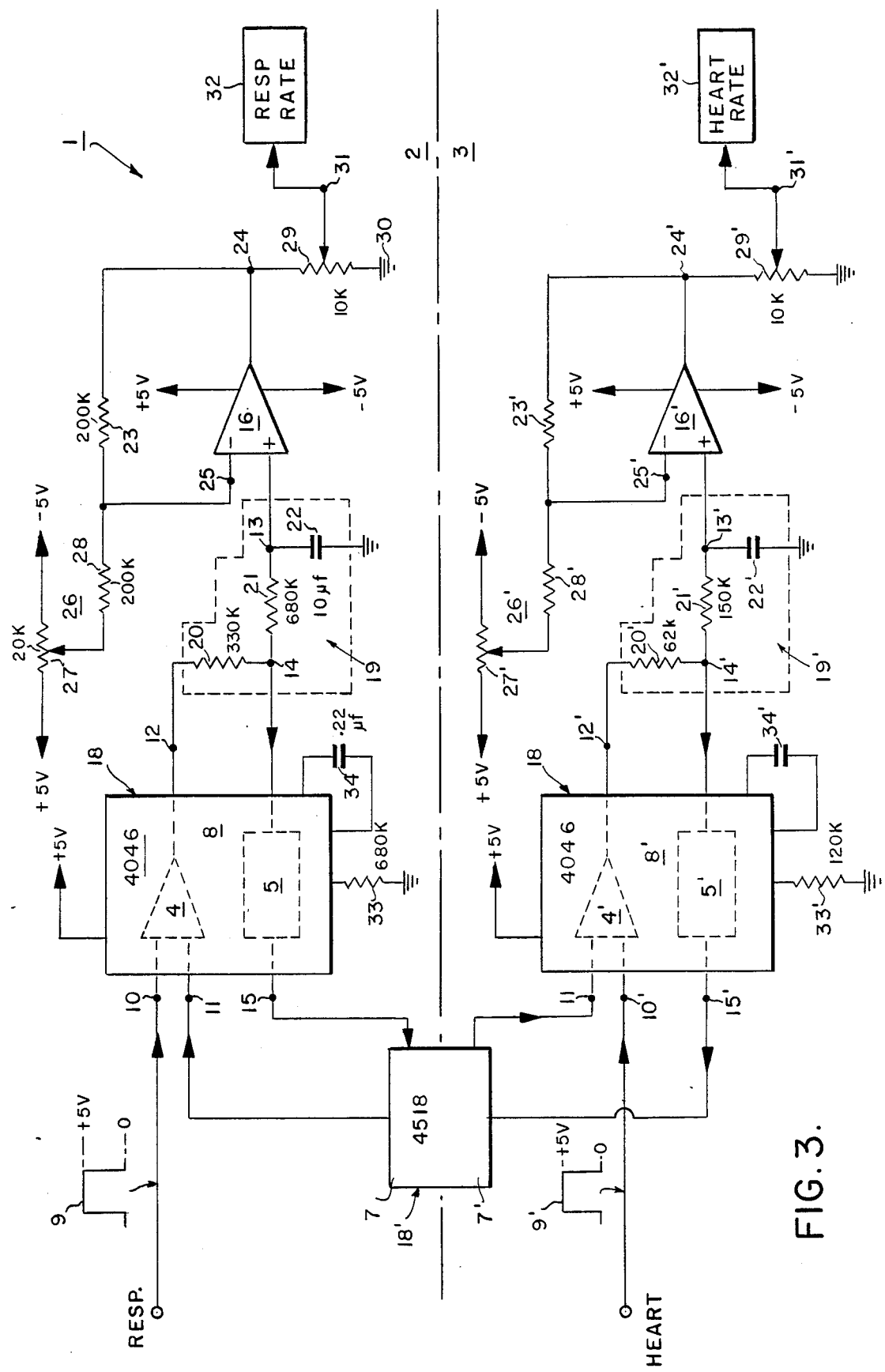
FIG. 3 is a preferred detailed circuit diagram.

A circuit diagram of a preferred embodiment of instrument 1 is shown in FIG. 3, wherein the same reference characters as in FIG. 1 are used whenever possible for the same parts.

The impedance pneumogram (IPG) and electrocardiogram (ECG) which are sensed via electrodes connected to the subject being monitored produce signals which, after they are amplified, filtered and detected, are the desired rectangular wave signals 9, 9' that represent the respiratory cycle rate of the subject and the heart beat rate, respectively. The specific techniques employed in sensing the IPG and ECG for producing signals 9 and 9' form no part of this invention and in themselves are well known in the bio-medical art.

Signal 9 is applied to the input terminal 10 of a CMOS No. 4046 IC PLL chip 18 produced by RCA, Motorola and others. This chip utilizes low power and detects the positive edges of the incoming pulses 9. Chip 18 is digital and includes a positive-edge triggered PC 4 and a VCO 5 which perform the functions previously described in connection with FIG. 1. Chip 18 is characterized by producing a substantially zero DC voltage at its output terminal 12 when signal 9 is removed from input terminal 10, by having a relatively fast response time, and by developing an output DC voltage at output terminal 12 which is linear over a relatively large range (greater than 10 to 1) of pulse rates, as shown in FIG. 2.

The output signal from terminal 12 is applied to a compensating lead-lag RC network 19 consisting of a resistor 20 connected in series with a resistor 21 and a capacitor 22. The junction between resistor 21 and capacitor 22 is connected to the positive input terminal 13 of an operational amplifier 16 having a negative feedback resistor 23 between its output terminal 24 and its negative input terminal 25. An offset network 26 consisting of a potentiometer 27 is connected between −5 volts and +5 volts. The amount of offset is controlled by a resistor 28 which is connected between potentiometer 27 and terminal 25. A portion of the amplified signal from amplifier 16 is obtained from the output of a potentiometer 29 connected between output terminal 24 and ground 30. The output terminal 31 of potentiometer 29 provides a DC voltage to a utilization device 32, such as a meter or recorder.

The DC voltage at terminal 31 is a linear translation of the respiratory rate signal 9 applied to input terminal 10. The lead lag network 19 provides to its terminal 13 a filtered output which is proportional to the rate being monitored. Network 19 also optimizes the response time and shape of the signal provided at output terminal 12 of chip 18.

Resistor 33 and capacitor 34 control the operating frequency of the VCO 5 on the IC chip 18. Since the frequency of the incoming signal 9 is relatively low, it is divided by ten in divider 7 to allow the VCO 5 on the chip 18 to operate at a higher frequency. Divider 7 is preferably an IC chip 18' sold commercially under No. 4518. As a consequence, resistor 33 and capacitor 34 can have relatively low values which reduce their cost, increase thermal stability and reduce noise.

It is important that amplifier 6 have a relatively high input impedance, say larger than ten times the sum of the impedances of resistors 20 and 21.

The output signal at terminal 31 is linear over at least a ten-to-one range (FIG. 2). Such linearity over such a wide range was heretofore obtainable only by the use of relatively complex and expensive circuits.

The heart beat circuit in channel 3 and the respiratory cycle circuit in channel 2 are substantially identical, except that the respiratory circuit is required to operate over a lower frequency range. Hence, no description of the heart beat circuit in channel 3 is herein provided, and similar components are designated with the same reference characters followed by a prime (').

The maximum rates for the respiration and heart signals were 64 breaths per minute and 255 beats per minute, which correspond to VCO frequencies of 10.7 and 42.5 Hz, respectively. The values of the components in the circuit are given on the drawing. These values can be obtained experimentally, with the aid of tables, and with the manufacturer's specifications for IC chips 18.

I claim:

1. A portable physiological rate measurement instrument for accurately measuring the rate of an unknown pulse wave over an extended range of rate values, said pulse wave having a frequency in the range of 0–4.25 hertz, said instrument comprising: a low powered phase-locked loop including a phase comparator, a filtering network, a voltage-controlled oscillator and a frequency divider arranged in series; said phase comparator having a first input responsive to said unknown pulse wave and a second input responsive to the output signal of said frequency divider; said phase comparator providing an output signal dependent on the difference in phase and frequency between the signals appearing on said first and second inputs, said output signal having a DC component and an AC component, said phase-locked loop including an integrated digital chip (4046) which consists of a positive-edge triggered phase comparator and a voltage-controlled oscillator and is characterized by producing at the output of the phase comparator a signal having a substantially zero amplitude when no pulse wave is applied to the first input of the phase comparator; said filter comprising an R-C network attached to the integrated digital chip to control the operating frequency of the voltage controlled oscillator, said filter being constructed and arranged to respond to a pulse train up to a frequency of 4.25 hertz; said network comprising a lead-lag RC network consisting of a first resistor having a first end connected to the output of the phase comparator and a second end connected to the input of the voltage controlled oscillator, and a second resistor having a first end connected to the second and so the first resistor and a second end connected to one end of a capacitor, said capacitor having another end connected to a voltage reference point; and a high-input impedance amplifier, the impedance being at least ten times the sum of the resistors of the lead-lag network, said amplifier having an input connected to the second end of said second resistor the amplifier being configured to provide flexible gain and offset adjustment for calibration, said amplifier having an output connected to a utilization device which measures the instantaneous rate of said pulse wave.

2. The instrument set forth in claim 1 in which there are two phase-locked loops, one for measuring respiratory rate and the other for measuring heart rate, the two phase-locked loops sharing a frequency divider comprising IC chip No. 4518.

* * * * *